U S010500835B2

(12) United States Patent
Matthews et al.

(10) Patent No.: US 10,500,835 B2
(45) Date of Patent: Dec. 10, 2019

(54) IN SITU MONITORING OF DIRECT INK WRITE PROCESS USING ELECTROMAGNETIC RESONANT COUPLING

(71) Applicant: Lawrence Livermore National Security, LLC, Livermore, CA (US)

(72) Inventors: Manyalibo Joseph Matthews, Livermore, CA (US); Eric Duoss, Danville, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 117 days.

(21) Appl. No.: 15/290,611

(22) Filed: Oct. 11, 2016

(65) Prior Publication Data

US 2018/0099461 A1 Apr. 12, 2018

(51) Int. Cl.
| | |
|---|---|
| *B33Y 50/02* | (2015.01) |
| *B29C 35/08* | (2006.01) |
| *B33Y 10/00* | (2015.01) |
| *B33Y 30/00* | (2015.01) |
| *B29C 64/00* | (2017.01) |
| *B29C 64/112* | (2017.01) |

(Continued)

(52) U.S. Cl.
CPC .......... *B33Y 50/02* (2014.12); *B29C 35/0805* (2013.01); *B29C 64/00* (2017.08); *B29C 64/106* (2017.08); *B29C 64/112* (2017.08); *B29C 64/209* (2017.08); *B29C 64/386* (2017.08); *B33Y 10/00* (2014.12); *B33Y 30/00* (2014.12); *B29C 2035/0811* (2013.01); *B29C 2035/0861* (2013.01); *B29K 2105/0058* (2013.01)

(58) Field of Classification Search
CPC ......... B33Y 50/02; B33Y 10/00; B33Y 30/00; B29C 64/112; B29C 64/386; B29C 64/209; B29C 64/00; B29C 64/106; B29C 35/0805; B29C 2035/0811; B29C 2035/0861; B29K 2105/0058
See application file for complete search history.

(56) References Cited

PUBLICATIONS

Jennifer A. Lewis et al., "Direct Ink Writing of Three-Dimensional Ceramic Structures", J. American Ceramic Society, 89 [12] 3599-3609 (2006); DOI: 10.1111/j.1551-2916.2006.01382.x.

(Continued)

*Primary Examiner* — Robert S Walters, Jr.
(74) *Attorney, Agent, or Firm* — Harness, Dickey & Pierce, PLC

(57) ABSTRACT

In the additive manufacturing process, a monitored or controlled mixture of materials is deposited to form an additive manufactured product by delivering the mixture of materials through a material flow path while using an excitation source to introduce electromagnetic energy into the material flow path using a circuit element having inductive or capacitive reactance disposed adjacent the material ejecting orifice. The excitation source produces an electromagnetic field condition within the material flow path that is responsive to at least one of the permeability and permittivity properties of a space within the material flow path. A sensing means coupled electrically or magnetically to the excitation means is responsive to the electromagnetic field condition and provides at least one control parameter based on the electromagnetic field condition that may be used to control the composition of the mixture of materials by adjusting proportions of constituent materials.

16 Claims, 4 Drawing Sheets

(51) Int. Cl.
  *B29C 64/209* (2017.01)
  *B29C 64/106* (2017.01)
  *B29C 64/386* (2017.01)
  *B29K 105/00* (2006.01)

(56) References Cited

PUBLICATIONS

Mohammad Vaezi et al., "A review on 3D micro-additive manufacturing technologies", Int J Adv Manuf Technol (2013) 67;1721-1754; DOI 10.1007/s00170-012-4605-2; published online: Nov. 25, 2012, Springer-Verlag, London, 2012.

Joseph Cesarano III et al., Recent Developments in Robocasting of Ceramics and Multimaterial Deposition, Sandia National Laboratories, Albuquerque, NM, 1998.

IN SITU MONITORING OF DIRECT INK WRITE PROCESS USING ELECTROMAGNETIC RESONANT COUPLING

FIELD

The present disclosure relates generally to direct ink writing (DIW) as an additive manufacturing technique. More particularly, the disclosure relates to techniques for verifying and/or controlling the composition of the ink material using electromagnetic resonant coupling to perform in situ material monitoring.

BACKGROUND

This section provides background information related to the present disclosure which is not necessarily prior art.

Direct-ink writing (DIW) is an additive manufacturing technique capable of creating micro-scale and macro-scale structures with extreme precision. It works well with a variety of materials, including mixtures and composites of materials derived from multiple sources.

In some applications the feedstock material (ink) can comprise multiple constituents. For example the feedstock can consist of a mixture of different chemical or structural components. In precision manufacturing it can be important to maintain precise control over the feedstock composition. Thus where two or more feedstock constituents are mixed upstream, precise control over the mixture is needed. In some applications, the mixture may need to be tuned in real time, as the additive manufacturing process is underway. In other applications, the mixture is prepared in advance, making it desirable to test, monitor or validate the composition to determine if the resultant manufactured product is within compositional tolerances.

While the ability to monitor and control the feedstock composition can be important in manufacturing both micro-scale and macro-scale products, doing so becomes quite a bit more difficult for micro-scale structures (e.g., structures having a scale in the sub-millimeter range, such as on the order of 150 microns or smaller). There are several reasons for this. First, the physical properties of micro-scale structures can be inherently more difficult to assess than with macro-scale structures. Second, even minute changes in the material delivery system can have a big impact on the composition of the manufactured product. Third, changes I ambient temperature and pressure conditions can effect significant changes in the composition.

SUMMARY

This section provides a general summary of the disclosure, and is not a comprehensive disclosure of its full scope or all of its features.

The present disclosure addresses the heretofore unsolved problems in additive manufacturing, by introducing an electromagnetic resonant coupling apparatus into the manufacturing system. The electromagnetic resonant coupling apparatus can be deployed where it can monitor the composition of the feedstock material in real time, as the additive manufacturing process is underway. The apparatus can be used both to generate and deliver a feedback signal that can control the feedstock mixture in real time, and to accurately monitor the feedstock composition for quality control and verification purposes. The electromagnetic resonant coupling apparatus can be deployed at or near the feedstock dispensing nozzle or tip, thus sensing the feedstock composition at or near the point where the actual manufactured product is being built. In this way, any changes in the upstream material delivery system can be detected and quickly compensated for.

The present disclosure describes several embodiments using electromagnetic resonant coupling to characterize the ink flowing through a DIW nozzle, which can be calibrated to yield quantitative information about ink composition as material is deposited. The disclosed technique is based on coupling electromagnetic fields into the ink, preferably near the nozzle orifice, using inductive coils or capacitors and detecting changes in coupling efficiency or resonant tuning using radio frequency (RF) electronics. The disclosed technique can be used to measure feedstock properties in situ during deposition for a number of processes including: direct ink write, polymer extrusion, fluid spraying, gas phase delivery systems and the like.

In accordance with one aspect, the disclosed apparatus for depositing a controlled mixture of materials to form an additive manufactured product includes a means for defining a material flow path and a means for delivering a controlled mixture of materials through said material flow path, where the constitution of the controlled mixture is established by manipulating at least one control parameter. The apparatus also includes an excitation means for introducing electromagnetic energy into the material flow path The excitation means produces an electromagnetic field condition within the material flow path that is responsive to at least one of the electromagnetic constitutive (permeability and permittivity) properties of a space within the material flow path. The apparatus further includes a sensing means coupled electrically or magnetically to the excitation means and responsive to the electromagnetic field condition. The sensing means provides the at least one control parameter based on the electromagnetic field condition.

In accordance with another aspect, a method of forming an additive manufactured product is disclosed. According to the method, an additive manufacturing material is delivered through a material flow path. Electromagnetic energy is introduced into the material flow path thereby producing an electromagnetic field condition within the material flow path, wherein the electromagnetic field condition is responsive to at least one of the permeability and permittivity properties of a space within the material flow path through which the additive manufacturing material flows. In this way the material may respond and be altered in situ through EM fields to affect the properties of the final deposited material. The method further includes sensing the electromagnetic field condition to provide a control parameter based on the electromagnetic field condition, and using the control parameter to perform in real time as the product is being formed at least one of: (a) change the constitution of the additive manufacturing material and (b) validate the quality of the additive manufactured product.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The present disclosure describes how electromagnetic resonant coupling may be used to monitor the direct ink write process, in situ. To this end, three embodiments are illustrated and described. However, it will be understood that these embodiments are merely intended to explain how to implement the electromagnetic resonant coupling technique, so that those of skill in the art will understand how to apply the technique in a particular application.

In this regard, it will be appreciated that direct ink writing for additive manufacturing can be implemented using wide variety of different mechanisms. Some DIW mechanisms are droplet-based (e.g., 3D printing, ink-jet printing, hot-melt ink-jet printing) where ink droplets, typically of a controlled size, are formed and launched by the ink jet head to produce the 3D object either by layered build-up of the ink material, or by using the ink material to bind another material. Other DIW mechanisms are filament-based DIW (robocasting in air, robocasting in oil, fused deposition, micropen writing) where a filament of material of a controlled diameter is extruded through a nozzle to deposit the material, in layers or otherwise, as required to define the 3D object.

In some DIW applications it can be advantageous or necessary to control the precise composition of the ink being deposited. This has heretofore been difficult because there has been no effective way of measuring the ink material, in situ, and particularly right at the point where the material is being deposited to form the printed object.

The present disclosure uses electromagnetic resonant coupling to measure the composition of the ink, by assessing changes in the permeability and/or permittivity of the ink material and comparing either to theory or to a set of composition calibration samples. As will be more fully described, an electromagnetic field is established in the material flow path, such as at a point in the flow path where measurement of the material constitution is desired. The measurement point may be, for example, at or near the orifice or tip of the dispensing nozzle or other dispensing structure.

As the material flows through this electromagnetic field, changes in material composition, or other material properties such as density, causes changes in the permeability and/or permittivity of the space where the electromagnetic field and the flow path intersect. These changes in permeability and/or permittivity are sensed by a sensing circuit that is magnetically or electrically coupled to the electromagnetic field in the measurement region.

Overview of the Electromagnetic Resonant Coupling System

Figure 1:
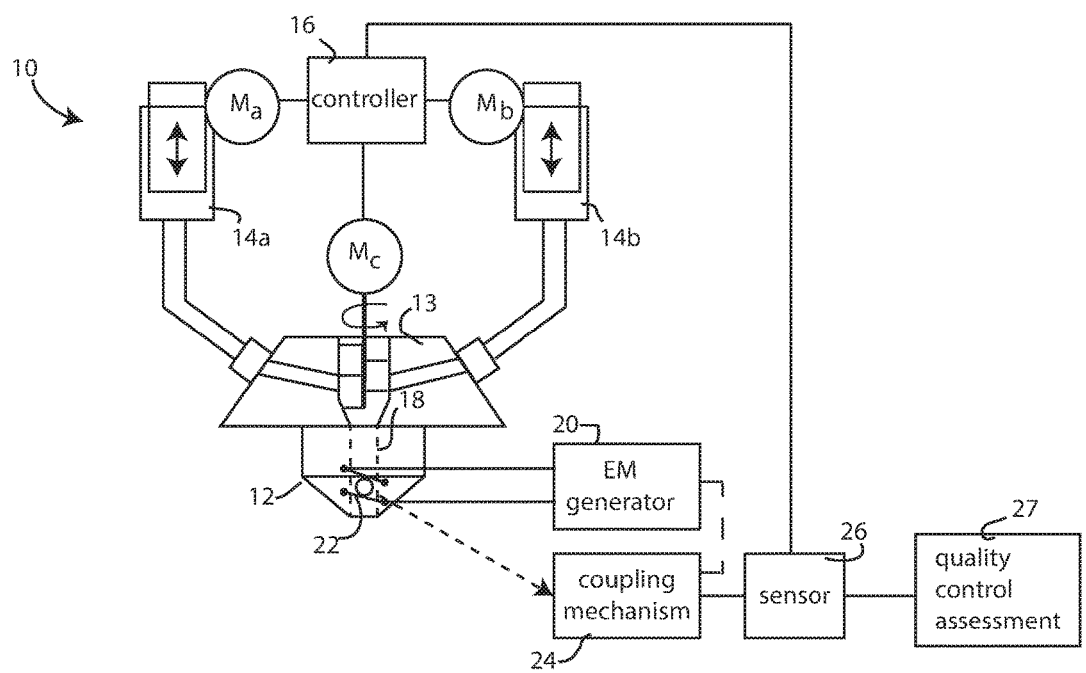
FIG. 1 is a block diagram of an additive manufacturing apparatus illustrating some of the concepts of the disclosed electromagnetic resonant coupling system.

Referring first to FIG. 1, an overview of the electromagnetic resonant coupling system 10 will be provided using an exemplary DIW additive manufacturing system having plural sources of ink material. For purposes of illustration, the DIW system includes a nozzle 12 supplied by a mixing head 13 that delivers ink material from plural sources, such as motor-controlled (by motors $M_a$ and $M_b$) syringes 14a and 14b that deliver material to a motor-controlled (by motor $M_c$) mixing screw or the like. The mixing head 13 and the syringes 14a and 14b are electronically controlled by a controller 16, which may be implemented by a microprocessor or microcontroller.

The nozzle 12 defines a material flow path 18 through which the ink material is delivered from the mixing head 13 to build up the additive manufactured product P. An electromagnetic generator 20 introduces electromagnetic energy into the flow path 18 by developing an electromagnetic field in a region that intersects with the flow path. The electromagnetic field may be developed by supplying electromagnetic energy to an inductor or coil 22 that surrounds the flow path. Thus the generator 20 and coil 22 define an excitation source for introducing electromagnetic energy into the material flow path. As illustrated, in this case the coil 22 is disposed near the tip or orifice end of the nozzle 12. Being situated near the tip, the electromagnetic resonant coupling system is adapted to measure the ink constitution near the tip, just prior to the ink being deposited to form the additive manufactured product.

A sensor 26 is electrically or magnetically coupled to the coil 22 through a suitable coupling mechanism 24, examples of which are discussed in connection with the various embodiments below. Being coupled to the electromagnetic field within the space that intersects the material flow path 18, the sensor 26 is able to respond to changes in the electromagnetic field condition. In particular the sensor 26 detects changes in permeability and/or permittivity within the space intersecting the material flow path 18. These changes are measured and fed as a control signal that may be supplied to controller 16 and used by the controller to adjust the respective components of the ink material.

Figure 2:
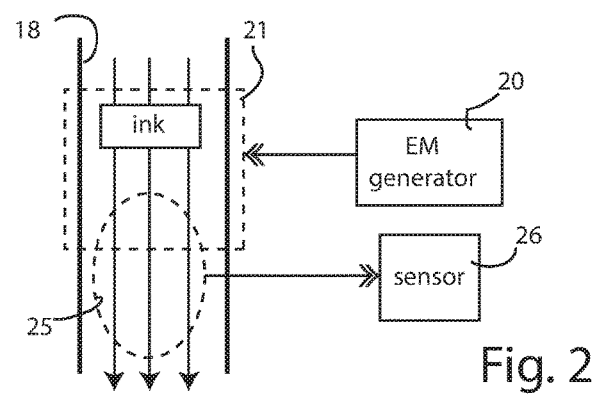
FIG. 2 is a diagrammatic view of a portion of the material flow path, illustrating the electromagnetic field and resonant coupling regions.

FIG. 2 provides a diagrammatic representation of the electromagnetic resonant coupling concept. Specifically, FIG. 2 illustrates a portion of the material flow path 18 through which the DIW ink material is flowing. The electromagnetic generator 20 injects electromagnetic energy into a region within the flow path, thereby establishing a field, illustrated diagrammatically at 21. It will be appreciated that the precise shape, nature and extent of this field will depend on the geometry of the structure used to inject the electromagnetic energy. For example, if a coil, such as coil 22 (FIG. 1) is used, the field will be a magnetic field having lines of flux that are concentrated through the longitudinal center of the coil. If a capacitor is used to inject the electromagnetic energy, the field will be an electric field having lines of force that span from one plate of the capacitor to the other.

Because the DIW ink material is flowing through the field of the injected electromagnetic energy, the dielectric properties (permeability and/or permittivity) of the ink material will change the propagation velocity of the electromagnetic energy within the space occupied by the field 21. This change in the electromagnetic energy is sensed by the electromagnetic resonant coupling apparatus. The relationship among permeability, permittivity and propagation velocity are discussed more fully below.

The disclosed electromagnetic resonance coupling technique uses a structure to electromagnetically couple to at least a portion of the space occupied by the field 21. This coupling region has been diagrammatically illustrated at 25. By coupling a sensor 26 to this overlapping coupling region 25, the effect of the material on the injected electromagnetic energy can be sensed. By analyzing the permeability and/or permittivity, the constitution or physical makeup of the ink material can be determined. In practical terms, the permeability is associated with inductive reactance and can thus be assessed by assessing changes in current flowing in an inductor positioned in the coupling region 25. Additionally, permittivity is associated with capacitive reactance and can thus be assessed by assessing changes in voltage across a capacitor positioned in the coupling region 25. Examples of both of these coupling techniques will be provided in the example embodiments next discussed.

First Embodiment

Figure 3:
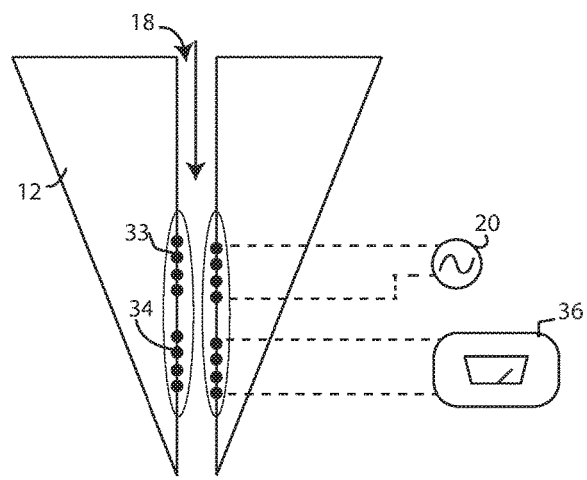
FIG. 3 is an additive manufacturing apparatus employing a first embodiment of the disclosed electromagnetic resonant coupling system.

Referring to FIG. 3, a first embodiment of an electromagnetic resonant coupling system that utilizes a pair of inductive coils: a first coil that injects an electromagnetic field into the measurement region and a second coil that senses the electromagnetic field condition by assessing the strength or amplitude of the sensed signal.

As illustrated, the nozzle 12 is provided with a first coil, which forms an inductive drive coil 33 that surrounds the material flow path 18. A second coil is also provided, which forms an inductive receiver coil 34, which is disposed adjacent the drive coil 33, and which also surrounds the material flow path 18. The electromagnetic generator 20 is implemented as a radio frequency (RF) signal generator that is electrically coupled to the inductive drive coil 33. The signal generator produces an oscillating current that flows through coil 33, producing a magnetic field that is magnetically coupled to the inductive receiver coil 34. Although different magnetic coupling arrangements are possible, as illustrated here, coils 33 and 34 are coaxially aligned and thus behave as a solenoid transformer wound about a common core that includes the material flow path 18. Thus any changes in permeability of the ink material within the flow path will change the inductance of the coils and thus change the degree to which a current is induced in the inductive receiver coil 34.

The inductive receiver coil 34 is, in turn, electrically coupled to an RF receiver circuit 36, which may include an RF amplifier and RF detector. The amplitude or signal strength of the receiver signal represents a measure of the degree to which coupling has occurred between the inductive drive coil 33 and the inductive receiver coil 34. Changes in this measure represent changes in inductance caused by changes in permeability. In other words, the strength of the coupling is proportional to the magnetic permeability, such that as the material composition changes during DIW deposition, the strength of the induced RF signal can be amplified at the receiver circuit 36 and used to measure these changes.

Second Embodiment

Figure 4:
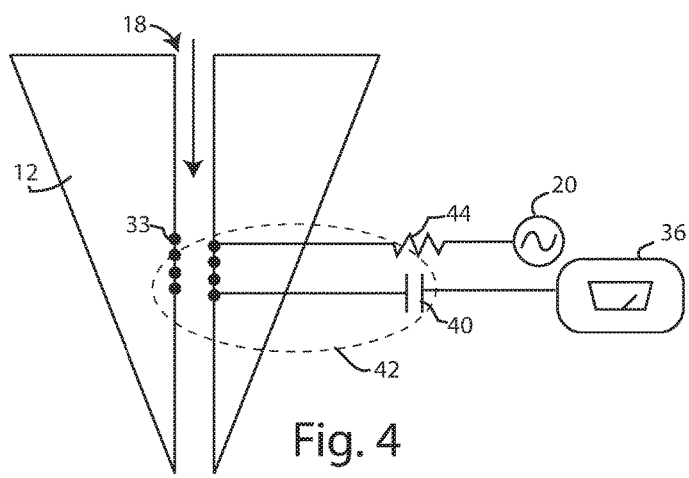
FIG. 4 is an additive manufacturing apparatus employing a second embodiment of the disclosed electromagnetic resonant coupling system.

Referring to FIG. 4, a second embodiment of an electromagnetic resonant coupling system that utilizes an inductive coil in the material flow path and that senses the electromagnetic field condition by monitoring the change in frequency of a resonant tank circuit (e.g., RLC circuit).

As illustrated, the nozzle 12 is provided with an inductive drive coil 33 that surrounds the material flow path 18. This inductive drive coil 33 is electrically coupled to a capacitor 40 to form a resonant tank circuit 42, which is electrically coupled through a suitable resistor 44 to the electromagnetic generator 20. In this case the electromagnetic generator 20 is implemented using a broadband signal generator that supplies energy to the tank circuit 42 causing the tank circuit to oscillate or ring at its characteristic frequency, dictated by the inductance of inductive drive coil 33 and capacitance of capacitor 40, according to the following equations:

$$f = \frac{1}{2\pi\sqrt{LC}} \qquad \text{Eq. 1}$$

where $$L = \frac{\mu N^2 A}{l + 0.45d} \qquad \text{Eq. 2}$$

In Eq. 1, L (the inductance of the inductive drive coil 33 disposed in the flow path 18) is directly proportional upon the permeability p of the material in the flow path 18, as described in Eqs. 2.

In Eq. 2, N corresponds to the number of turns of the inductive drive coil 33, A corresponds to the cross-sectional area of the inductive drive coil, l is the length of the inductive drive coil and d is the diameter of the inductive drive coil.

As the ink material flows through the material flow path 18, the permeability within the region intersected by the flow path and the electromagnetic field will change as the material constitution changes. This change in permeability changes the inductance of inductive drive coil 33, which in turn changes the resonant frequency of the tank circuit 42.

In this embodiment, the sensor 26 is implemented using a frequency detector. The frequency detector can be implemented using a frequency counter or other suitable phase-frequency detector circuit.

Third Embodiment

Figure 5:
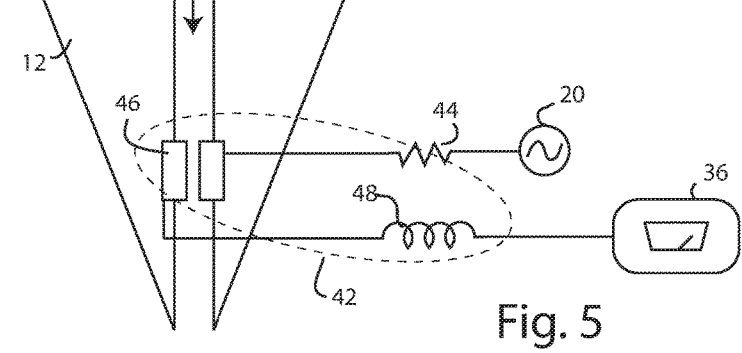
FIG. 5 is an additive manufacturing apparatus employing a third embodiment of the disclosed electromagnetic resonant coupling system.

Referring to FIG. 5, a third embodiment of an electromagnetic resonant coupling system utilizes a capacitive device in the material flow path and senses the electromagnetic field condition by monitoring the change in frequency of a resonant tank circuit (e.g., RLC circuit).

Figure 6:
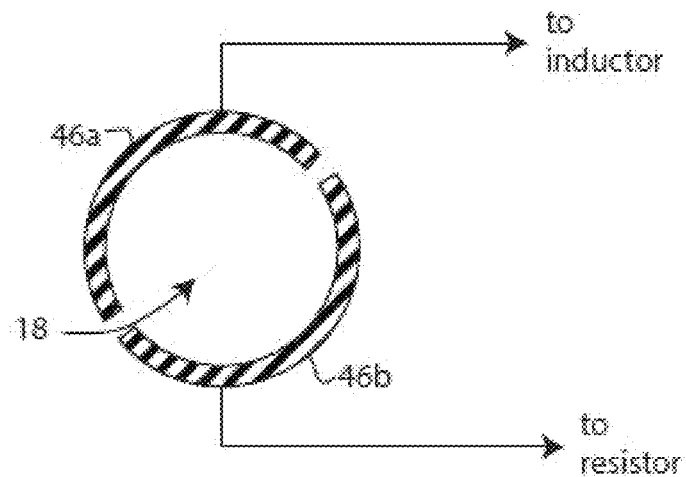
FIG. 6 is a cross sectional view of the cylindrical capacitor of the embodiment of FIG. 5.

As illustrated, the nozzle 12 is provided with a capacitor 46 that surrounds the material flow path 18. If desired a cylindrical capacitor, such as illustrated in FIG. 6, may be used. As illustrated in FIG. 6, the cylindrical capacitor has two arcuate plates 46a and 46b that surround the material flow path 18. This capacitor is electrically coupled to an inductor coil 48 to form a resonant tank circuit 42 which is electrically coupled through a suitable resistor 44 to the electromagnetic generator 20. In this case, as with the second embodiment, the electromagnetic generator 20 can be implemented using a broadband signal generator that supplies energy to the tank circuit 42 causing the tank circuit to oscillate or ring at its characteristic frequency, dictated by the capacitance of capacitor 46 and the inductance of inductor 48, according to the following equations.

$$f = \frac{1}{2\pi\sqrt{LC}} \qquad \text{Eq. 3}$$

$$C + \frac{\varepsilon A}{s} \qquad \text{Eq. 4}$$

In Eq. 3, C (the capacitance of the capacitor 46 disposed in the flow path) is directly proportional upon the permittivity E of the material in the flow path, as described in Eq. 4. In Eq. 4, A is the area of either of the two capacitor plates, and s is the spacing. Those of skill in the art will appreciate that Eq. 3 states the general case of a simple parallel plate capacitor. The cylindrical capacitor featured in the third embodiment shown in FIG. 6 would have a somewhat more complex relationship because the spacing s is not constant in that case. Even in that case, however, the capacitance C is still proportional to the permittivity.

As the ink material flows through the material flow path 18, the permittivity within the region intersected by the flow path 18 and the electromagnetic field will change as the material constitution changes. This change in permittivity changes the capacitance of capacitor 46 which in turn changes the resonant frequency of the tank circuit 42.

In this embodiment, as with the second embodiment, the sensor 26 is implemented using a frequency detector. The frequency detector can be implemented using a frequency counter or other suitable phase-frequency detector circuit.

One skilled in the art will recognize that variations and combinations (e.g. using resonant LC circuits in the variation shown in FIG. 2) can be used, including use of lock-in amplifier approaches involving coupling driver and sensor (as illustrated by the dashed line coupling between EM generator 20 and coupling mechanism 24 in FIG. 1), all resulting in different levels of coupling and sensitivity of the device.

Figure 8:
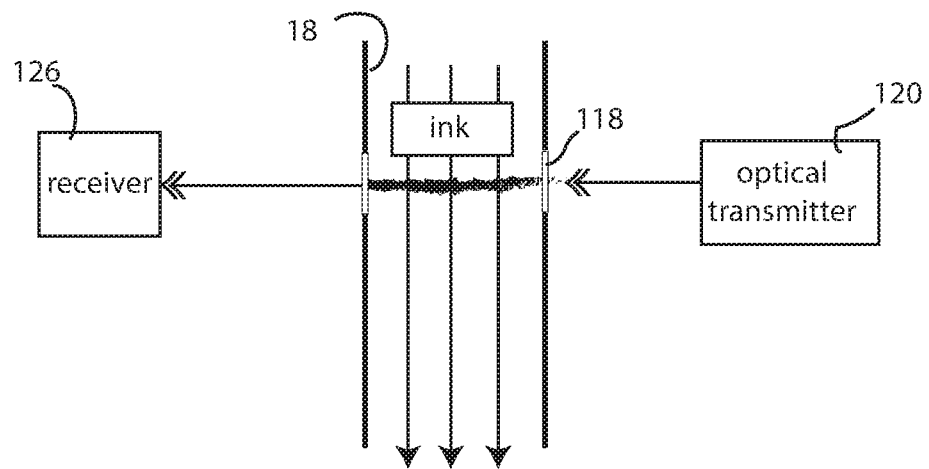
FIG. 8 is a diagrammatic view of an alternate embodiment that uses electromagnetic energy at an optical wavelength.

While the foregoing embodiments have utilized electromagnetic energy generally at radio frequency wavelengths, the disclosed concepts are also applicable at optical wavelengths, including infrared and ultraviolet wavelengths. An exemplary optical embodiment is illustrated in FIG. 8. In the optical embodiment the nozzle sidewalls are transparent at the utilized optical wavelength, or include an optically transparent window 118.

The illustrated embodiment of FIG. 8 employs an optical transmitter-receiver pair (transmitter 120, receiver 126) that senses optical signal attenuation as the illumination passes through the fluid stream of ink material. Alternatively or additionally, the optical transmitter-receiver pair may also sense resonance conditions due to optical absorption by the ink material. Thus changes in the receiver 126 output are indicative of changes in the electromagnetic constitutive properties of the fluid stream of ink material within the material flow path 18.

Consideration of Feedstock Micro-Scale Material Properties

The disclosed electromagnetic resonant coupling apparatus and method is well suited to respond to minute changes in permeability and/or permittivity of the feedstock material as it travels through the material flow path for deposition to form the manufactured product.

Figure 7:
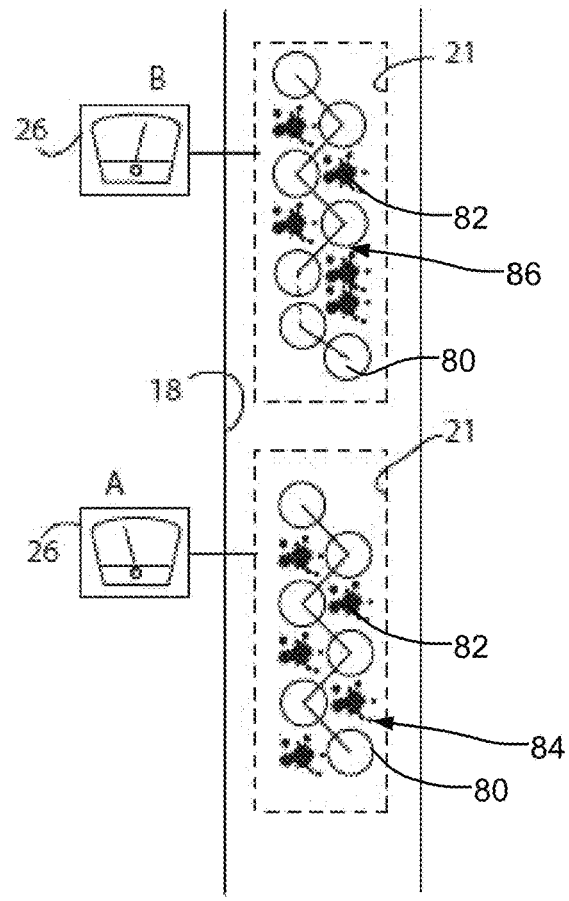
FIG. 7 is a diagrammatic representation of a micro-scale composite feedstock flowing through the material flow path, being sensed by the electromagnetic resonant coupling apparatus.

In a micro-scale structure, such as the structure diagrammatically illustrated in FIG. 7, the microstructures and the electrostatic and magnetic properties of the materials that comprise the feedstock will effect often subtle, yet measurable changes in the electromagnetic field through which the material flows. In FIG. 7, a first constituent material 80 defines a microscopic lattice structure that forms interstitial regions supporting a second constituent material 82.

As illustrated at 84, when the lattice structure defines a first configuration, the electromagnetic field 21 exhibits a measurable permeability and/or permittivity state that results in reading A on sensor 26. By comparison, as illustrated at 86, when the lattice structure defines a second configuration, the electromagnetic field 21 exhibits a measurable permeability and/or permittivity state that results in reading B on sensor 26. In some cases the second lattice configuration 86 could represent a defect in the normal lattice structure shown at 84. Alternatively, the second lattice configuration 86 could represent a different state or lattice arrangement, or a different molecular anomer, for example. Thus some measurable difference may not represent a structural defect. Whether by defect or intent, the different physical geometries of the materials can have a measurable effect on the electromagnetic field existing in the space occupied by the material which the electromagnetic resonant coupling apparatus is capable of measuring.

In addition to differences in physical geometries, the materials themselves may also have distinct electrostatic, ferromagnetic, ferrimagnetic, paramagnetic and diamagnetic properties that can have a measurable effect on the electromagnetic field. In this regard, the electrostatic properties that influence permittivity are exhibited in many materials, based on their outer atomic shell electron configuration. Magnetic properties that influence permeability are exhibited in materials based on whether the outer atomic shell electrons are paired or unpaired. If unpaired, the material has paramagnetic properties that draw the material towards a magnetic field; if paired, the material has diamagnetic properties that repel the material away from a magnetic field. In addition, certain elements such as cobalt and iron, as well as certain compounds containing those elements exhibit strong ferromagnetic properties.

Regarding the micro-scale and RF frequencies, it bears noting that wavelengths in the range of constituent feature length scale inside the fluid flow should be particularly sensitive, due to Mie scattering, i.e., 1-200 um or Terahertz to Infrared.

Relationship Among Permeability, Permittivity and Propagation Velocity

Some of the above-described embodiments interact primarily with the permeability and magnetic properties of the feedstock material (e.g., the first and second embodiments). Other embodiments interact primarily with the permittivity and electrostatic properties of the feedstock material (e.g., third embodiment). However, in all cases the electromagnetic field injected into the measurement region has both an electric field component and a magnetic field component. These two field components exist together whenever there is an electric charge that is moving at an accelerating rate (such as a charge moving in an oscillating fashion, thus exhibiting angular acceleration). Moreover, as described in Maxwell's equation (Eq. 5 below), the electromagnetic energy produced by an accelerating charge exhibits an electromagnetic field that propagates in a self-perpetuation fashion.

$$\oint B \cdot dl = \mu_0 I + \varepsilon_0 \mu_0 \frac{d\Phi_E}{dt} \qquad \text{Eq. 5}$$

The above equation represents the case where the electromagnetic energy is propagating through free space (devoid of matter). Thus such field is influenced by the magnetic permeability $\mu_0$ and electrostatic permittivity $\varepsilon_0$ of free space.

These magnetic and electrostatic properties of free space are defined in terms of propagation velocity of the electromagnetic wave in free space, namely the speed of light.

$$c^2 = \frac{1}{\mu_o \varepsilon_o} \qquad \text{Eq. 6}$$

When electromagnetic energy propagates through a space containing matter, the propagation speed decreases, corresponding to permeability and permittivity values that differ from those of free space. Thus when that electromagnetic wave propagates through a space containing matter, the propagation velocity decreases in inverse proportion to the permeability and/or permittivity of the matter.

As a consequence of the electric and magnetic fields being integrally related, the interaction of the electromagnetic field with the feedstock material can be sensed using either the electric field or the magnetic field. As noted above, the embodiments of FIGS. 2 and 3 use an inductive receiver coil that responds to the magnetic field. Thus these embodiments are most adept at sensing changes in permeability, although changes in permittivity would have an effect on the electric field and this effect would have a potentially measurable impact on the magnetic field. The embodiment of FIG. 4 uses a capacitor that responds to the electric field. Thus this embodiment is most adept at sensing changes in permittivity, although changes in permeability would have an effect on the magnetic field and this effect would have a potentially measurable impact on the electric field.

Those of skill in the art will appreciate that there are other structures that can be used to sense changes in permeability and/or permittivity of the feedstock material. By way of non-limiting example, the feedstock material can be feed through a waveguide or transmission line into which the electromagnetic field has been injected. Changes in the propagation velocity through the waveguide or transmission line can then be sensed either directly, or by detecting changes in resonant frequency (as with the tuned tank circuit), or by detecting position of nodes and antinodes in standing waves produced along the length of the waveguide or transmission line.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An apparatus for depositing a controlled mixture of materials to form an additive manufactured product, comprising:
    a means for defining a material flow path;
    a means for delivering a controlled mixture of materials through said material flow path, where a constitution of the controlled mixture is established by manipulating at least one control parameter;
    an excitation means for introducing electromagnetic energy into the material flow path;
    the excitation means producing an electromagnetic field condition within the material flow path that is responsive to at least one of the permeability and permittivity properties of a space within the material flow path;
    a sensing means coupled electrically or magnetically to the excitation means and responsive to the electromagnetic field condition;
    the sensing means providing the at least one control parameter based on the electromagnetic field condition.

2. The apparatus of claim 1 wherein the means for defining a material flow path is defined by a nozzle having an orifice through which the controlled mixture is ejected for forming the additive manufactured product.

3. The apparatus of claim 2 wherein the means for introducing electromagnetic energy into the material flow path comprises an inductor disposed about the nozzle.

4. The apparatus of claim 3 wherein the inductor is disposed about the nozzle adjacent the orifice.

5. The apparatus of claim 2 wherein the means for introducing electromagnetic energy into the material flow path comprises a capacitor having plates disposed about the nozzle.

6. The apparatus of claim 5 wherein the capacitor plates are disposed about the nozzle adjacent the orifice.

7. The apparatus of claim 1 wherein the means for introducing electromagnetic energy into the material flow path comprises a circuit component having inductive or capacitive reactance.

8. The apparatus of claim 1 wherein the excitation means comprises an electromagnetic frequency generator.

9. The apparatus of claim 1 wherein the excitation means comprises a broadband signal generator.

10. The apparatus of claim 1 wherein the means for introducing electromagnetic energy into the material flow path comprises a first inductor and the sensing means comprises a second inductor magnetically coupled to the first inductor.

11. The apparatus of claim 1 wherein the means for introducing electromagnetic energy into the material flow path comprises an inductor and the sensing means comprises a capacitor coupled to the inductor to define a tank circuit.

12. The apparatus of claim 1 wherein the means for delivering a controlled mixture of materials includes at least one valve that is electrically controlled by the sensing means.

13. The apparatus of claim 1 wherein the means for delivering a controlled mixture of materials includes at least one valve that is electrically controlled by the sensing means in real time as the additive manufactured product is being formed.

14. The apparatus of claim 1 wherein the constitution of the controlled mixture is established before the additive manufactured product is formed and wherein the sensing means provides the at least one control parameter to validate the quality of the additive manufactured product in real time as the product is being formed.

15. The apparatus of claim 1 wherein the excitation means produces electromagnetic energy of at least one optical wavelength and wherein the means for defining a material flow path includes a window structure that is optically transparent at the at least one optical wavelength.

16. The apparatus of claim 1 wherein the means for introducing electromagnetic energy into the material flow path comprises a capacitor and the sensing means comprises an inductor coupled to the capacitor to define a tank circuit.

* * * * *